(12) United States Patent
Newhauser, Jr. et al.

(10) Patent No.: US 10,806,849 B2
(45) Date of Patent: Oct. 20, 2020

(54) DEVICES AND METHODS FOR TRANSNASAL IRRIGATION OR SUCTIONING OF THE SINUSES

(71) Applicant: Acclarent, Inc., Irvine, CA (US)

(72) Inventors: Richard R. Newhauser, Jr., Redwood City, CA (US); Eric A. Goldfarb, Belmont, CA (US); John W. White, Menlo Park, CA (US); Arthur M. Lin, Fremont, CA (US)

(73) Assignee: Acclarent, Inc., Irvine, CA (US)

( * ) Notice: Subject to any disclaimer, the term of this patent is extended or adjusted under 35 U.S.C. 154(b) by 0 days.

(21) Appl. No.: 15/498,907

(22) Filed: Apr. 27, 2017

(65) Prior Publication Data

US 2017/0224907 A1 Aug. 10, 2017

Related U.S. Application Data

(62) Division of application No. 13/549,828, filed on Jul. 16, 2012, now abandoned.

(60) Provisional application No. 61/511,320, filed on Jul. 25, 2011.

(51) Int. Cl.
*A61M 3/02* (2006.01)
*A61B 17/24* (2006.01)
*A61M 25/00* (2006.01)

(52) U.S. Cl.
CPC .......... *A61M 3/0279* (2013.01); *A61B 17/24* (2013.01); *A61M 3/0283* (2013.01); *A61M 25/0054* (2013.01)

(58) Field of Classification Search
CPC ... A61B 17/24; A61M 3/0279; A61M 3/0283; A61M 25/007; A61M 25/008; A61M 25/0052; A61M 25/0053; A61M 25/0054; A61M 2210/0681; A61M 3/0208
See application file for complete search history.

(56) References Cited

U.S. PATENT DOCUMENTS

| | | | |
|---|---|---|---|
| 5,380,307 A * | 1/1995 | Chee | A61M 25/0054 604/264 |
| 5,817,058 A | 10/1998 | Shaw | |
| 7,645,272 B2 | 1/2010 | Chang et al. | |
| 7,654,997 B2 | 2/2010 | Makower et al. | |
| 7,803,150 B2 | 9/2010 | Chang et al. | |

(Continued)

FOREIGN PATENT DOCUMENTS

| WO | WO 2008/091652 | 7/2008 |
|---|---|---|
| WO | WO 2010/033629 | 3/2010 |

OTHER PUBLICATIONS

International Search Report dated Mar. 8, 2013, International Application No. PCT/US2012/046919, filed Jul. 16, 2012.

*Primary Examiner* — Tiffany Legette
(74) *Attorney, Agent, or Firm* — Todd J. Burns (57) ABSTRACT

An irrigation catheter for the treatment of the sinus anatomy is described. The catheter comprises a proximal portion, a rigid middle portion, and a flexible distal portion. The flexible distal portion comprises an irrigation tip and the proximal portion has a stiffness that is intermediate the stiffness of the rigid middle portion and the flexible distal portion. The irrigation tip has a tip opening and one or more radially facing openings. A method for irrigating or suctioning the sinus anatomy includes inserting an irrigation catheter into a patient's anatomy and irrigating or suctioning a target space.

9 Claims, 4 Drawing Sheets

(56) References Cited

U.S. PATENT DOCUMENTS

| | | |
|---|---|---|
| 2001/0041881 A1 | 11/2001 | Sarge |
| 2005/0043712 A1* | 2/2005 | Devens, Jr. ........ A61M 25/0009 |
| | | 604/525 |
| 2006/0004323 A1 | 1/2006 | Chang et al. |
| 2006/0063973 A1 | 3/2006 | Makower et al. |
| 2006/0095066 A1 | 5/2006 | Chang et al. |
| 2007/0123813 A1 | 5/2007 | Barbut |
| 2007/0129751 A1* | 6/2007 | Muni ..................... A61B 17/24 |
| | | 606/196 |
| 2007/0250105 A1 | 10/2007 | Ressemann |
| 2008/0097391 A1* | 4/2008 | Feinberg .......... A61B 17/00491 |
| | | 604/523 |
| 2008/0097400 A1 | 4/2008 | Chang et al. |
| 2008/0183128 A1 | 7/2008 | Morriss et al. |
| 2008/0195041 A1* | 8/2008 | Goldfarb ............... A61M 29/02 |
| | | 604/96.01 |
| 2008/0306428 A1* | 12/2008 | Becker ................ A61F 9/00772 |
| | | 604/8 |
| 2009/0024072 A1 | 1/2009 | Criado et al. |
| 2009/0124999 A1 | 5/2009 | Horton et al. |
| 2010/0152706 A1 | 6/2010 | Morris |
| 2012/0071856 A1 | 3/2012 | Goldfarb et al. |

* cited by examiner

DEVICES AND METHODS FOR TRANSNASAL IRRIGATION OR SUCTIONING OF THE SINUSES

FIELD OF THE INVENTION

The present invention relates, in general, to medical devices and, in particular, to medical devices and related methods for the treatment of sinus conditions.

BACKGROUND OF THE INVENTION

The paranasal sinuses are hollow cavities in the skull connected by small openings, known as ostia, to the nasal canal. Each ostium between a paranasal sinus and the nasal cavity is formed by a bone covered by a layer of mucosal tissue. Normally, air passes into and out of the paranasal sinuses through the ostia. Also, mucus is continually formed by the mucosal lining of the sinuses and drains through the ostia and into the nasal canal.

Sinusitis is a general term that refers to inflammation in one or more of the paranasal sinuses. Acute sinusitis can be associated with upper respiratory infections or allergic conditions, which may cause tissue swelling and temporarily impede normal trans-ostial drainage and ventilation of the sinuses, thereby resulting in some collection of mucus and possibly infection within the sinus cavities. Chronic sinusitis is a long term condition characterized by persistent narrowing or blockage of one or more sinus ostia, resulting in chronic infection and inflammation of the sinuses. Chronic sinusitis is often associated with longstanding respiratory allergies, nasal polyps, hypertrophic nasal turbinates and/or deviated internasal septum. While acute sinusitis is typically caused by infection with a single pathogen (e.g., one type of bacteria, one type of virus, one type of fungus, etc.), chronic sinusitis is often associated with multiple pathogen infections (e.g., more than one type of bacteria or more than one genus of micro-organism).

Chronic sinusitis, if left untreated, can result in irreparable damage to the tissues and/or bony structures of the paranasal anatomy. The initial treatment of chronic sinusitis usually involves the use of drugs such as decongestants, steroid nasal sprays and antibiotics (if the infection is bacterial). In cases where drug treatment alone fails to provide permanent relief, surgical intervention may be indicated.

The most common surgical procedure for treating chronic sinusitis is functional endoscopic sinus surgery (FESS). FESS is commonly performed using an endoscope and various rigid instruments inserted through the patient's nostril. The endoscope is used to visualize the positioning and use of various rigid instruments used for removing tissue from the nasal cavity and sinus ostia in an attempt to improve sinus drainage.

A technique known as the Balloon Sinuplasty™ procedure and a system for performing the procedure has been developed by Acclarent Inc, of Menlo Park, Calif. for treatment of sinusitis. A number of US patents and patent applications including U.S. Pat. Nos. 7,645,272, 7,654,997, and 7,803,150 describe various embodiments of the Balloon Sinuplasty™ procedure as well as various devices useable in the performance of such procedure. In the Balloon Sinuplasty™ procedure, a guide catheter is inserted into the nose and positioned within or adjacent to the ostium of the affected paranasal sinus. A guidewire is then advanced through the guide catheter and into the affected paranasal sinus. Thereafter, a dilation catheter having an expandable dilator (e.g. an inflatable balloon) is advanced over the guidewire to a position where the dilator is positioned within the ostium of the affected paranasal sinus. The dilator is then expanded, causing dilation of the ostium and remodelling of bone adjacent to the ostium, without required incision of the mucosa or removal of any bone. The catheters and guidewire are then removed and the dilated ostium allows for improved drainage from and ventilation of the affected paranasal sinus.

Before or after performing a FESS or Balloon Sinuplasty™ procedure, it may be useful or necessary to suction or irrigate the paranasal sinus. A device described in US 2008/0183128 may be used for irrigating a paranasal sinus. The irrigation catheter may be advanced through a guide catheter and into an ostium or the sinus for purposes of, for example irrigation, suctioning, substance delivery and culture retrieval.

There is a continuing need for improved methods and devices for treating the paranasal sinus. Although the irrigation catheter described above is easy to use, it would be useful to provide an improved catheter for irrigating or suctioning the sinuses before or after the Balloon Sinuplasty™ procedure.

SUMMARY OF THE INVENTION

In a first aspect, the invention is an irrigation catheter for the treatment of a sinus, the catheter having an irrigation lumen, and further having a proximal portion, a rigid middle portion and a flexible distal portion. The flexible distal portion has an irrigation tip and the proximal portion has a stiffness that is intermediate the stiffness of the rigid middle portion and the flexible distal portion.

In one embodiment, the irrigation tip has a tip opening. There may be one or more radially facing openings. In a particular embodiment, there may be 3 radially facing openings. In a further embodiment the radially facing openings may have a diameter of between 0.020 inches and 0.050 inches, or they may have a diameter of 0.026 inches.

In another embodiment the rigid middle portion of the irrigation catheter may contain a stiffening member that surrounds the irrigation lumen. The stiffening member may be a hypotube. In addition, the catheter proximal portion may contain a nylon sleeve that surrounds the irrigation lumen.

In a further embodiment, the irrigation catheter may have one or more direct visualization markers or one or more radiographic markers. Further, a dual use connector may further be included. The connector may be a y-connector or a valve. The rigid middle portion may further include an actuator.

In a further aspect, the invention is a system for treatment of a target space in the nasal anatomy having a handle, a guide catheter for attachment to the handle, and an irrigation catheter with an outer diameter that is smaller than the inner diameter of the guide catheter. The irrigation catheter has an irrigation lumen and further has a proximal portion, a rigid middle portion; and a flexible distal portion with an irrigation tip, the proximal portion having a stiffness that is intermediate the stiffness of the rigid middle portion and the flexible distal portion In a further embodiment, the system having a handle, a guide catheter, and an irrigation catheter, may have a luer connector on the irrigation catheter. In one embodiment, the luer connector may have a slanted positioner. A guidewire may further be included.

In another aspect, the invention is a method for treating a target space in the nasal anatomy. The method involves positioning an irrigation catheter having an irrigation lumen and further having a proximal portion, a rigid middle portion and a flexible distal portion in the nasal anatomy. The flexible distal portion has an irrigation tip and the proximal portion has a stiffness that is intermediate the stiffness of the rigid middle portion and the flexible distal portion. The method further involves connecting a fluid source to the irrigation catheter and delivering fluid to the target space from the fluid source though the irrigation catheter.

In another embodiment the method includes the delivering the fluid at a flow rate of between 50 ml/min and 200 ml/min or between 75 ml/min and 125 ml/min.

In a further embodiment of the method, the target space is selected from the group consisting of the frontal sinus, the maxillary sinus, the ethmoid sinus, and the sphenoid sinus opening.

In yet another embodiment of the method, the fluid is selected from the group consisting of water, saline, contrast agents, antimicrobial agents anti-inflammatory agents, decongestants, mucous thinning agents, anesthetic agents, analgesic agents, anti-allergenic agents, allergens, anti-proliferative agents, hemostatic agents, cytotoxic agents, and biological agents or combinations of any of the above.

In a third aspect, the invention is a method for treating a target space in the nasal anatomy. The method involves positioning an irrigation catheter having an irrigation lumen and further having a proximal portion, a rigid middle portion and a flexible distal portion in the nasal anatomy. The flexible distal portion has an irrigation tip and the proximal portion has a stiffness that is intermediate the stiffness of the rigid middle portion and the flexible distal portion. The method further involves connecting a vacuum source to the irrigation catheter and suctioning the target space though the irrigation lumen.

In another embodiment of the method, the target space is selected from the group consisting of the frontal sinus, the maxillary sinus, the ethmoid sinus, and the sphenoid sinus opening.

In another aspect, the invention is an irrigation catheter for the treatment of a sinus, the catheter having an irrigation lumen, and further having a proximal portion, a rigid middle portion and a flexible distal portion. The flexible distal portion has an irrigation tip and the middle portion has an actuator.

In one embodiment, the proximal portion has is a rigid proximal portion and further includes an irrigation connector. In a further embodiment the actuator has a distal actuator flange and a proximal actuator flange. In another embodiment, the irrigation tip has a tip opening and one or more radially facing openings.

In another embodiment the rigid middle portion of the irrigation catheter may contain a stiffening member that surrounds the irrigation lumen. In addition, the catheter proximal portion may contain a stiffening member that surrounds the irrigation lumen.

In a further aspect, the invention is a system for treatment of a target space in the nasal anatomy having a handle, a guide catheter for attachment to the handle, and an irrigation catheter with an outer diameter that is smaller than the inner diameter of the guide catheter. The irrigation catheter has an irrigation lumen and further has a proximal portion, a rigid middle portion; and a flexible distal portion with an irrigation tip, the middle portion further having an actuator. In one embodiment, the proximal portion has is a rigid proximal portion and further includes an irrigation connector. In a further embodiment the actuator has a distal actuator flange and a proximal actuator flange. In another embodiment, the irrigation tip has a tip opening and one or more radially facing openings. In another embodiment the rigid middle portion of the irrigation catheter may contain a stiffening member that surrounds the irrigation lumen. In addition, the catheter proximal portion may contain a stiffening member that surrounds the irrigation lumen.

In another aspect, the invention is a method for treating a target space in the nasal anatomy. The method involves positioning an irrigation catheter having an irrigation lumen and further having a proximal portion, a rigid middle portion and a flexible distal portion in the nasal anatomy. The flexible distal portion has an irrigation tip and the middle portion has an actuator. The method further involves connecting a fluid source to the irrigation catheter and delivering fluid to the target space from the fluid source though the irrigation catheter. In another embodiment the method includes the delivering the fluid at a flow rate of between 50 ml/min and 200 ml/min. In a further embodiment of the method, the target space is selected from the group consisting of the frontal sinus, the maxillary sinus, the ethmoid sinus, and the sphenoid sinus opening.

In yet another embodiment of the method, the fluid is selected from the group consisting of water, saline, contrast agents, antimicrobial agents anti-inflammatory agents, decongestants, mucous thinning agents, anesthetic agents, analgesic agents, anti-allergenic agents, allergens, anti-proliferative agents, hemostatic agents, cytotoxic agents, and biological agents or combinations of any of the above.

In a further aspect, the invention is a method for treating a target space in the nasal anatomy. The method involves positioning an irrigation catheter having an irrigation lumen and further having a proximal portion, a rigid middle portion and a flexible distal portion in the nasal anatomy. The flexible distal portion has an irrigation tip and the middle portion has an actuator. The method further involves connecting a vacuum source to the irrigation catheter and suctioning the target space though the irrigation lumen. In another embodiment of the method, the target space is selected from the group consisting of the frontal sinus, the maxillary sinus, the ethmoid sinus, and the sphenoid sinus opening.

DETAILED DESCRIPTION

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

Medical devices according to embodiments of the present invention are beneficial in that, for example, their configuration provides for a particularly efficient preparation and treatment of a patient's sinus and is mechanically simple. Moreover, the simplicity of the medical devices provides for them to be manufactured in a cost effective manner. In addition, the medical device according to embodiments of the present invention is sufficiently stiff that it can be beneficially employed to access sinus anatomy followed by a convenient suction and/or irrigation of the sinus.

Figure 1:
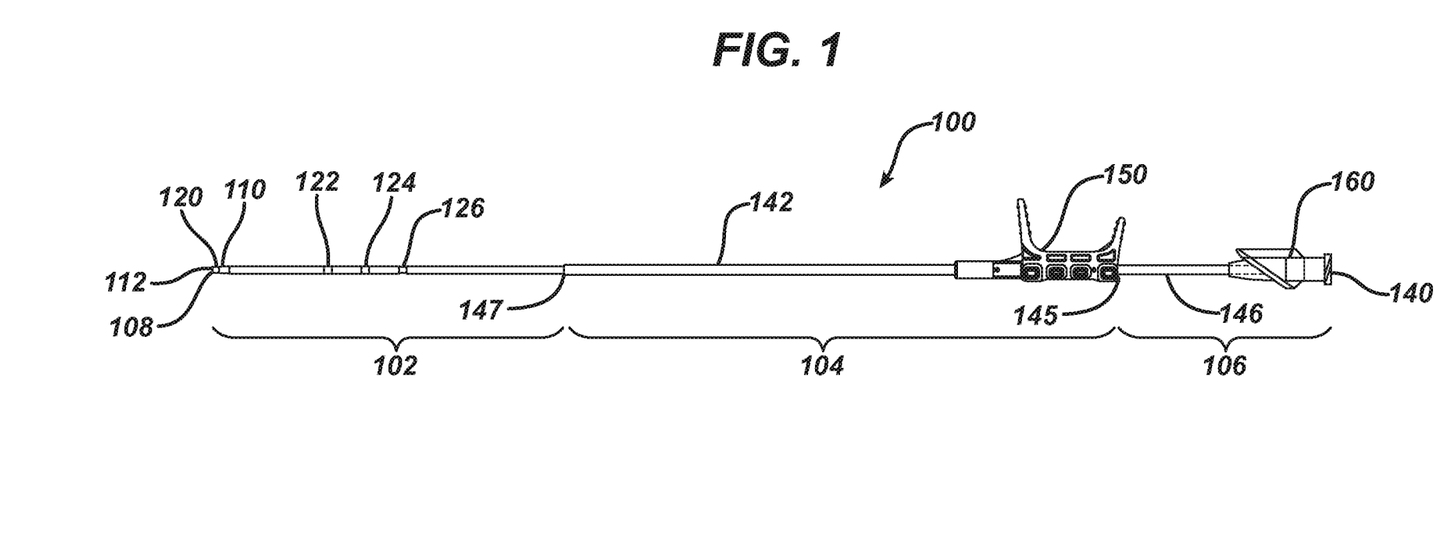
FIG. 1 is a simplified side view of a medical device according to an embodiment of the present invention.

FIG. 1 is a simplified side view of an irrigation catheter 100 for the treatment of a sinus (for example a frontal sinus, maxillary sinus, ethmoid sinus, or sphenoid sinus) according to an embodiment of the present invention. The sinus irrigation catheter 100 has a flexible distal portion 102 and a rigid middle portion 104 and a proximal portion 106 with a stiffness that is intermediate the flexible distal portion 102 and the rigid middle portion 104.

Figure 2:
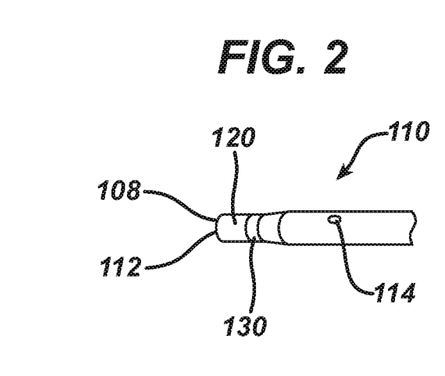
FIG. 2 is an enlarged view of the distal end of the medical device shown in FIG. 1.

The flexible distal portion 102 of the sinus irrigation catheter 100 will now be described in greater detail. Referring now to FIG. 2, and enlarged view of the irrigation tip 110 can be seen with both a forward facing tip opening 112 and radially facing openings 114 to provide a means to irrigate from within a target sinus for diagnostic or therapeutic purposes. By radially facing openings, is intended that the flow through the openings may be at 90 degrees from the flow through the tip opening, but it may also be at other angles such as 30, 45 or 60 degrees or other angles between 0 and 90 degrees. The irrigation catheter 100 is designed to irrigate the sinus through the tip opening 112 and the three radially facing openings 114 in the irrigation tip 110. Further, instead of delivering fluid, a vacuum may be applied and a culture may be obtained by suctioning through with the tip opening 112 or the radially facing openings 114.

As shown in FIG. 1 in some embodiments, direct visualization markers and/or radiographic markers may be disposed along the flexible distal portion 102. Generally, "direct visualization markers" refers to markers that may be viewed during use with the naked eye or by use of an endoscope, while radiographic markers include radiopaque material and are viewed using a radiographic device such as intra-operative fluoroscopy. In one embodiment, a first distal direct visualization marker 120, which has a distal edge aligned with the distal end of the irrigation tip 110 and is colored white for easy visualization and a radiographic marker 130 is disposed over the first distal direct visualization marker 120, the radiographic marker 130 including a radiopaque material that can be viewed using a radiographic device such as intraoperative fluoroscopy.

Direct visualization markers can be positioned in a number of locations along the flexible distal portion 102 of the sinus irrigation catheter 100. Although one embodiment is described here with reference to FIG. 1, other variations may be substituted in alternative embodiments. In one embodiment, flexible distal portion 102 may have a dark color, such as black, dark blue, dark grey or the like or may be transparent, and markers may have a light color, such as white, green, red or the like. In some embodiments, markers may have different colors and/or different widths to facilitate distinguishing the markers from one another during use. This contrast in colors may facilitate viewing the markers in a darkened operation room and/or when using an endoscope inside a patient in the presence of blood.

A second direct visualization marker 122 is disposed on the flexible distal portion 102 such that the middle of the marker is 3 cm apart from the proximal end of the first direct visualization marker 120. Visualization of this marker 122 indicates to the user that 3 cm of the flexible distal portion 102 has exited into the target anatomy. In one embodiment, the second distal direct visualization marker 122 may be about 2 mm wide and green in color, while the first marker 120 is about 2 mm and white in color. Of course, any of a number of different size and color combinations may be used alternatively.

A third direct visualization marker 124 is disposed on the flexible distal portion 102 such that the middle of the marker is 1 cm apart from the middle of the second direct visualization marker 122. Visualization of this marker 124 indicates to the user that a further 1 cm of the flexible distal portion 102, or a total of 4 cm of the flexible distal portion 102, has exited into the target anatomy. In one embodiment, the third direct visualization marker may be about 2 mm wide and white in color, while the second marker 122 is about 2 mm and green in color. Of course, any of a number of different size and color combinations may be used alternatively.

A fourth direct visualization marker 126 is disposed on the flexible distal portion 102 such that the middle of the marker is 1 cm apart from the middle of the third direct visualization marker 124. Visualization of this marker 126 indicates to the user that a further 1 cm of the flexible distal portion 102, or a total of 5 cm of the flexible distal portion 102, has exited into the target anatomy. As shown in FIG. 1, the fourth distal shaft marker is a double marker to distinguish the third and fourth distal shaft markers 124 and 126 one from one another. In one embodiment, the two markers forming the fourth distal shaft marker 126 are each 0.75 mm wide and white in color, however, the size and color of the marker can be changed in alternative embodiments. The differences in the direct visualization markers' color, length and number of marks give the indication of the relative location proximal to the sinus under endoscopic visibility. Using an endoscope, the physician user can identify the length of catheter that has been advanced and retracted and/or can approximate a location of the catheter 100 relative to patient anatomy such as a paranasal sinus ostium, other paranasal sinus opening, or other openings in the ear, nose or throat. Of course, in alternative embodiments, distal shaft markers having different numbers, sizes, colors and positions along the catheter shaft may be used. Referring again to FIG. 1, the irrigation tip 110 is made of a white extrusion that is fused to the inside of the flexible distal portion 102. Although the illustrative example shows this irrigation tip 110 to be a white extrusion, any color may be useful to distinguish the tip 110 from the remainder of the flexible distal portion 102. The flexible distal portion 102 defines the irrigation lumen 140 and is made of a flexible, biocompatible polymer material, such as nylon, polyethylene, polyether ether ketone (PEEK), or polyether block amides (e.g. Pebax for example). In the embodiment shown in FIG. 1, the material is Pebax. The material is preferably clear such that the physician user can see materials being delivered to a target location of a sinus anatomy, as well as being removed from the anatomy. The clear material also allows for visual trouble-shooting of the device, e.g. should the catheter 100 become clogged the user can visualize where the clog has occurred.

The rigid middle portion 104 of the catheter 100 includes a stiffening member 142, and in a particular embodiment this member is a 304 stainless steel hypotube shaft that surrounds the Pebax irrigation lumen 140. The proximal portion 106 of the catheter 100 is a combination of materials, a nylon sleeve 146 disposed about the pebax irrigation lumen 140. The three sections of disparate stiffness (the Pebax flexible distal portion 102, the hypotube and Pebax rigid middle section 104 and the nylon and Pebax proximal portion of intermediate stiffness 106) provide for ease of insertion of the irrigation catheter into and navigation through the tortuous sinus anatomy. Further, the physician user may be able to hold or support the catheter 100 by grasping just one location on the rigid middle section 104. Additionally, the middle portion 104 and the proximal portion 106 will maintain axial alignment when not being otherwise stressed (as, for example, when being inserted into the single-handed device described below with regard to FIG. 6).

Figure 3:
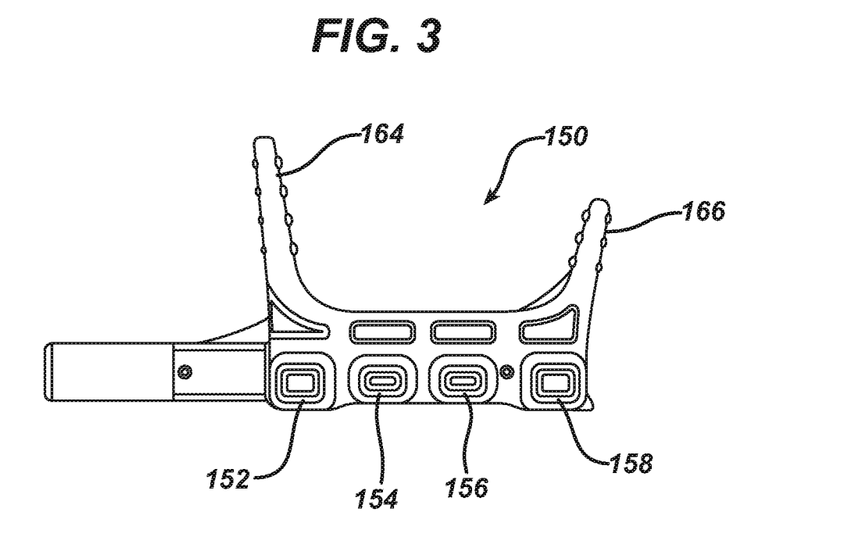
FIG. 3 is an enlarged view of the actuator of the medical device shown in FIG. 1.

The rigid middle portion 104 has a proximal end 145 and a distal end 147. At its proximal end 145, as shown in FIG. 3, the rigid middle portion 104 further includes an actuator 150. The actuator 150 contains treads 152, 154, 156, and 158 to provide a grip feature when the irrigation catheter is used as an individual unit, and as sliding surfaces which engaged in a handle (as described further below). These treads are shown on one side of the actuator 150, but are duplicated on the other side of the actuator 150. In the embodiment shown in FIG. 3, there are 4 treads on each side of the actuator 150, but there can be 2, 3, 4, 5, 6 or more treads as well. In FIG. 3, the first tread 152 and the last tread 158 may contact a handle for minimization of sliding friction and maximization of the direction between contacting surfaces for maximum stability within the handle. The distal actuator flange 164 and the proximal actuator flange 166 are shown with ridges on either side of the flanges. Insertion of the guide catheter 100 into the nasal anatomy can be effected by a thumb or single finger of the physician user as pressure is applied on the flange, pulling it toward the nasal anatomy. Similarly, removal from the nasal anatomy can be effected by the thumb or single finger of the physician user as pressure is applied on the flange, pushing it away from the nasal anatomy. Such telescoping operation enables single handed insertion of the catheter 100 and irrigation of the sinuses.

Figure 4:
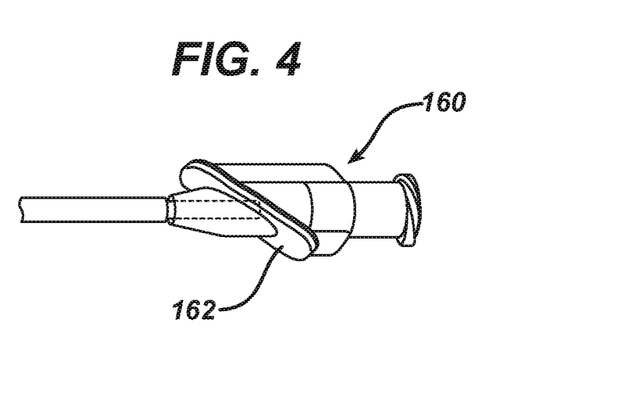
FIG. 4 is an enlarged view of the distal end of the medical device shown in FIG. 1.

A luer connector 160 connects the proximal end of the proximal portion 106 of irrigation catheter 100 to a source of irrigation or suction. In the embodiment shown in FIG. 4, a 45 degree slanted positioner 162 allows for ease of use with the single handled sinus treatment device described below with regard to FIG. 6. A syringe (e.g., having a volume of about 10 cc to about 60 cc, for example) may be connected to luer connector 160 The syringe may be used to drive the irrigation fluid out of the openings 112 and 114 by hand pressure by the operator on a hand pushable plunger of the syringe. Fluid pressures of about 4 to about 6 pounds per square inch (psi) are typically generated when using a 60 cc syringe, and pressures of about 15 to about 25 psi can be generated using a 10 cc syringe. Alternatively, the luer connector 160 may be connected to a high pressure valve which is in turn connected to a high pressure inflation device. The high pressure inflation device, that may be a screw-threaded pump of a type that can be used to inflate balloon catheters, has a screw-threaded plunger that can be torqued (or, alternatively, a rack and pinion driving mechanism can be substituted) to develop high pressure within a reservoir that contains an irrigation fluid (e.g., saline or other irrigating fluid used in ear, nose and throat practice), and locked via a locking mechanism to maintain the high pressure until it is released by opening the valve. Other types of high pressure pumps could be substituted, including motor-driven pumps.

Instead of or addition to use of the catheter 100 for irrigation the sinuses, as noted earlier, the catheter may be used to suction materials from within the sinuses. For use solely to suction the sinuses, a suction source such as a vacuum pump or other suction system may be connected to the luer connector 160. For use of the catheter for both irrigating and suctioning the sinuses, a dual-use connector such as a valve or Y-connector may be connected to the luer connector 160 to enable switching between the irrigation source and the suction source.

In one embodiment, the valve that is connected to the luer connector 160 and to a high pressure inflation device may be a high pressure push-button valve that is normally closed, but opens upon depressing a push-button. Of course, other alternative types of valves can be substituted as long as they are rated for sufficiently high pressure and are operable between closed and open states. Once the irrigation catheter 100 has been appropriately placed in a target where it is desired to perform the high pressure irrigation, pressure is built up in the reservoir by advancing a plunger, while the valve remains closed. Once sufficient pressure has been established (e.g., pressures of about 50 to 100 psi, or about 100 to 150 psi, or about 150 to 300 psi, or pressures greater than about 25 psi can be generated), the valve is opened, and a high pressure spray is impulsively driven and jets out of openings 112 and 114, developing vortices of flow in directions circumferentially around irrigation tip 110 to provide a scrubbing type of wash to the walls of the sinus cavity to remove debris, mucus, fungus, etc. The irrigation flow rate is approximately 100 ml/min and may be between about 50 and 200 ml/min or between about 75 and 125 ml/min with a maximum flow rate of 250 ml/min.

Irrigation catheter 100 is configured to irrigate and suction fluids deep within the sinuses, as well as other areas within the paranasal space. Irrigation catheter 100 is sized appropriately to be delivered into adult as well as pediatric sinuses, including maxillary, sphenoid, ethmoid and frontal sinuses. Irrigation catheter 100 can also be used to deliver diagnostic or therapeutic substances into the sinuses or other areas in the paranasal space. Examples of such diagnostic or therapeutic substances include, but are not limited to: contrast agents, pharmaceutically acceptable salt or dosage form of an antimicrobial agent (e.g., antibiotic, antiviral, antiparasitic, antifungal, etc.), a corticosteroid or other anti-inflammatory (e.g., an NSAID), a decongestant (e.g., vasoconstrictor), a mucous thinning agent (e.g., an expectorant or mucolytic), an anesthetic agent with or without vasoconstrictor (e.g., Xylocaine with or without epinephrine, Tetracaine with or without epinephrine), an analgesic agent, an agent (anti-allergenic agent) that prevents of modifies an allergic response (e.g., an antihistamine, cytokine inhibitor, leucotriene inhibitor, IgE inhibitor, immunomodulator), an allergen or another substance that causes secretion of mucous by tissues, anti-proliferative agents, hemostatic agents to stop bleeding, cytotoxic agents e.g. alcohol, and biological agents such as protein molecules, stem cells, genes or gene therapy preparations.

Referring now to FIG. 1, in one embodiment, the irrigation catheter may include a forward facing tip opening 112 and three radially facing openings 114 on irrigation tip 110 spaced 120 degrees apart, with the inner diameter of the forward facing tip opening being 0.037 inches and each of the side openings having a inner diameter of 0.026 inches. In the illustrative embodiment, the inner diameter of the distal portion 102 of the irrigation tip 110 at the position of the side openings that is proximal to the distal visualization marker 120 is about 0.042 inches. Alternative embodiments may include any suitable alternative number of side openings distributed in any suitable pattern such as a helical pattern. In one embodiment, a first side opening may be placed at about 5 mm.±0.0.5 mm from the distal end 108 of medical device 100, a second side opening may be placed at about 6 mm.±0.0.5 mm from the distal end 108 of medical device 100, and a third side opening may be placed at about 7 mm.±0.0.5 mm from the distal end 108 of medical device 100, with each of these measurements being from the distal end to approximately the center of each side opening. Each side opening may have any suitable diameter in various alternative embodiments. For example, in one embodiment, each side opening may have a diameter of between about 0.020 inches and about 0.050 inches or between about 0.030 inches and about 0.040 inches and or about 0.033 inches. In an alternative embodiment, the medical device 100 may contain an integrated guidewire such that there is no irrigation from the distal end of the device, but only from the radially facing openings.

Figure 5:
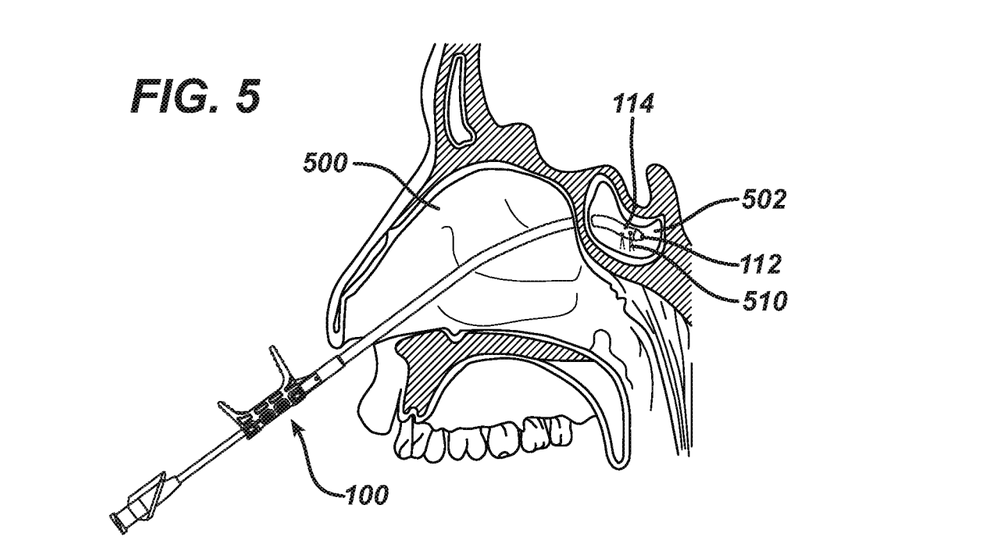
FIG. 5 is an illustration of a partial sagital sectional view through a human head showing the use of an irrigation catheter as described herein to perform at least one of irrigation, suction, and delivery of a therapeutic or diagnostic substance or retrieval of a culture.

FIG. 5 is an illustration of partial sagital sectional view through a human head showing access to a paranasal sinus by an irrigation system as described herein to perform at least one of irrigation, suction, or delivery of a therapeutic or diagnostic substance or retrieval of a culture. In FIG. 5, the sinus irrigation catheter 100 is introduced through a nostril and through a nasal cavity 500 to a location close inside of a sphenoid sinus 502. For other harder to reach anatomical locations, such as the maxillary sinus, for example, a sinus guide may be used. For accessing a maxillary sinus, a sinus guide having a bend of 110 degrees may be needed. Sinus guides may be straight, malleable, or may incorporate one or more preformed curves or bends as further described in U.S. Patent Publication Nos. 2006/004323; 2006/0063973; and 2006/0095066, for example, each of which are incorporated herein by reference in their entireties.

The distal end of irrigation catheter is inserted deep into sinus 502 so that tip opening 112 and radially facing openings 114 are positioned into any portion of the sinus anatomy, but in many cases may be positioned well within the sinus cavity to perform at least one of the functions noted above. Further, two functions, such as irrigation and suction may be performed with the irrigation system described herein. FIG. 5 illustrates an irrigation procedure being performed, as irrigation fluid 510 is jetted through the openings 112 and 114 to establish vortices to clean the walls of the sinus by the irrigation flow.

It is further noted that irrigation systems described herein are not limited to only being delivered through a natural anatomic pathway, but can also be delivered though a surgical opening to irrigate, suction, deliver therapeutic and/or diagnostic substances and/or take cultures. For example, a hole may be trephined to provide direct access to the frontal sinus and an irrigation system as described herein can be delivered through the hole to flush a frontal sinus. This technique can be particularly useful for a sinus that does not communicate normally with the middle meatus. As another example, the anterior wall of the ethmoid bulla can be punctured and an irrigation system as described herein can be inserted therethrough to flush the anterior ethmoid sinuses. This procedure may be done after removal of an ethmoid sinus stent, for example. An irrigation system described herein can be delivered through a maxillary antrostomy or Caldwell-Luc incision to perform any of the above described functions. Still further, an irrigation system as described herein may be delivered through the Eustachian tube or an incision to access the middle ear to perform any of the above-described functions in the location of the middle ear.

Delivery of an irrigation system, with or without use of a guide catheter may be additionally or alternatively visualized by using an endoscope or by using fluoroscopy, electromagnetic or optical guidance, including 3-dimensional visualization such as CT or MRI visualization or other known visualization techniques.

In many of the embodiments described above, an irrigation catheter 100 may be delivered into a sinus with or without a guidewire. The catheter 100 may be delivered over a guidewire, or the guidewire may be incorporated into the irrigation catheter 100. To deliver an irrigation catheter over a guidewire, for example, a distal end of the guidewire may first be advanced into a sinus through a guide catheter, as described above and in a number of the patent applications previously incorporated by reference. Systems including guide catheters (Relieva or Relieva Flex Sinus Guide Catheters), guidewires (Relieva Sinus Guidewire or Relieva Luma or Luma Sentry Guidewires) and handles (Relieva Sidekick Sinus Guide Catheter Handle) may be purchased from Acclarent Inc, Menlo Park, Calif. In one embodiment, the proximal end of a Relieva Sinus Guide Catheter is inserted into the fitting of a Relieva Sidekick Sinus Guide Catheter Handle. The guide catheter has an inner diameter that is greater than the outer diameter of the irrigation catheter. The guide catheter is placed near the target anatomy, a guidewire is advanced through the guide catheter and the irrigation catheter 100 may be advanced through the guide catheter and over the wire into the target anatomy. The irrigation catheter may be introduced absent the guidewire or the guidewire may be inserted into the irrigation catheter and the guidewire and irrigation catheter may be inserted into the guide catheter and positioned at the target anatomy.

Placement of a guidewire in a desired position in a sinus may be confirmed by fluoroscopy. Once the guidewire is in position, the irrigation catheter 100 may be advanced over the guidewire to position a distal portion of the catheter in the sinus. In various embodiments, the irrigation catheter may be advanced over the guidewire through a guide catheter or, alternatively, over the guidewire without using a guide catheter. Positioning of a distal portion of the irrigation catheter in the desired sinus may be confirmed using fluoroscopy, in embodiments where the irrigation catheter distal portion includes a radiopaque marker or material. In some embodiments, the guidewire may then be withdrawn through the irrigation catheter. Irrigation fluid may then be introduced through the irrigation catheter, and in some embodiments fluid may be suctioned back through the irrigation catheter. In various embodiments, any other suitable guidewire-based delivery techniques may be employed to advance an irrigation catheter of the present invention.

Figure 6:
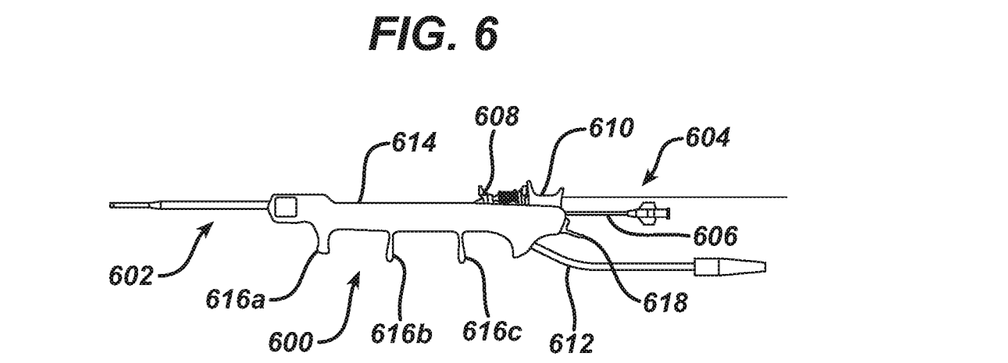
FIG. 6 is a side view of a medical device for the treatment of a sinus opening according to an embodiment of the present invention.
Figure 7:
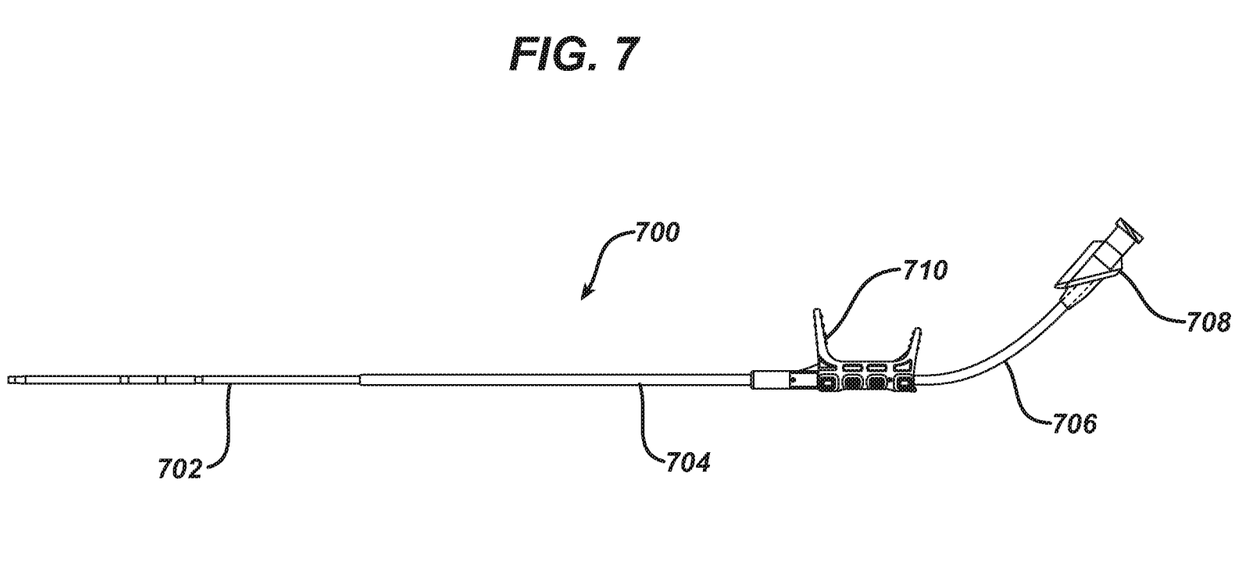
FIG. 7 is a simplified side of a medical device according to an alternative embodiment of the present invention.

These procedures may be performed as stand-alone procedures, or they may be follow-up procedures performed after performing some other procedure such as a dilation of the ostium. A medical device 600 for treating a sinus opening is shown in FIG. 6. This device 600 is further described in United States Publication No. 2012/0071856 and incorporated herein by reference in its entirety. The medical device 600 for the treatment of a sinus opening includes a guide catheter 602, a guide wire 604, a balloon catheter 606, a guide wire movement mechanism 608, a balloon catheter movement mechanism 610, and a suction pathway 612. The handle 614 is ergonomically designed such that the finger anchoring pegs 616a, 616b and 616c can be placed between the fingers of either a right handed or left handed user to provide for support of the device 600. The locking tab 618 prevents the balloon catheter mechanism 610 from moving proximally when it is in the up position, but allows for movement distally. When the locking tab 618 is in the down position, the balloon catheter 606 and guide wire 604 can be removed such that an irrigation catheter 100 can be inserted into the handle 614 and through the guide catheter 602. The 45 degree slanted positioner 162 on the semi-flexible tubing 106 allows the proximal portion 106 to slide above the proximal end of the handle 614 without interference so that the luer 160 can be positioned above the handle 614 and connected to a vacuum or fluid source. The distal end of the sinus irrigation catheter 100 is positioned at the dilated sinus ostium for irrigation, suction, or delivery of a therapeutic or diagnostic substance or retrieval of a culture. Other embodiments of the proximal portion 106 that would allow for positioning of the luer 160 above the handle 614 would include a permanently deformable proximal portion 106 or a hook or other attachment mechanism that could be connected to the proximal portion 106 to position the proximal portion 106 above the handle 614. Such an embodiment is shown in FIG. 7. In this embodiment, the distal portion 702 of the sinus irrigation catheter 700 is flexible as described earlier to provide for ease of insertion and navigation through the tortuous sinus anatomy. The middle portion 704 of the sinus irrigation catheter 700, also as described earlier is rigid such that it easily be held and supported and can be telescoped into a guide catheter (not shown) in a single handed operation by pushing or pulling actuator 710 distally toward the guide catheter. In this embodiment, the proximal portion 706 has a rigidity similar to the middle portion 704 such that the proximal portion 706 forms a hook (in this case, a curved hypotube) that positions the irrigation connector, luer 708, above the remainder of the catheter 700. In this way, the luer 708 is positioned above the device handle 614 shown in FIG. 6 and single handed operation of the catheter 700 is enabled without interference by the irrigation or suction system.

The invention has been described with reference to certain examples or embodiments of the invention, but various additions, deletions, alterations and modifications may be made to those examples and embodiments without departing from the intended spirit and scope of the invention. For example, any element or attribute of one embodiment or example may be incorporated into or used with another embodiment or example, unless otherwise specified or if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A system for treatment of a target space in a nasal anatomy, said system comprising: a handle; a guide catheter for attachment to the handle, said guide catheter having an inner diameter; and an irrigation catheter having an outer diameter, the outer diameter of the irrigation catheter being smaller than the inner diameter of the guide catheter, wherein said irrigation catheter has an irrigation lumen, said irrigation catheter comprising a proximal portion, a rigid middle portion comprising a hypotube stiffening member; and a flexible distal portion having an irrigation tip, said proximal portion having a stiffness that is intermediate a stiffness of said rigid middle portion and said flexible distal portion, wherein the system further comprises one or more direct visualization markers.

2. The system of claim 1 further including a guidewire.

3. The system of claim 1 wherein the proximal portion comprises a nylon sleeve that surrounds the irrigation lumen.

4. The system of claim 1 wherein the irrigation catheter further comprises one or more radiographic markers.

5. The system of claim 1 wherein the rigid middle portion further comprises an actuator.

6. The system of claim 1 wherein the proximal portion comprises a luer connector.

7. The system of claim 6 wherein the luer connector comprises a slanted positioner.

8. The system of claim 1 wherein the irrigation tip comprises a tip opening and one or more radially facing openings.

9. The system of claim 8 wherein the one or more radially facing openings comprise 3 openings.

* * * * *